United States Patent [19]

Wolff

[11] Patent Number: 4,911,162
[45] Date of Patent: Mar. 27, 1990

[54] TOURNIQUET

[76] Inventor: Stephen H. Wolff, 222 E. 35th St., New York, N.Y. 10016

[21] Appl. No.: 240,843

[22] Filed: Sep. 2, 1988

[51] Int. Cl.⁴ ............................................. A61B 17/12
[52] U.S. Cl. .................................. 606/203; 24/129 D
[58] Field of Search ............................. 128/169–171, 128/325–327, 876; 24/16 PB, 30.5 P, 118, 129 A, 129 D, 129 R, 324, 662, 130; 119/96, 101

[56] References Cited

U.S. PATENT DOCUMENTS

| 2,803,253 | 8/1957 | Campbell | 128/327 |
| 3,492,995 | 2/1970 | Ceravolo | 128/327 |
| 3,910,280 | 10/1975 | Talonn | 128/327 |

FOREIGN PATENT DOCUMENTS 0235628  6/1925  United Kingdom ................ 128/327

Primary Examiner—Michael H. Thaler
Assistant Examiner—William Lewis
Attorney, Agent, or Firm—Lerner, David, Littenberg, Krumholz & Mentlik

[57] ABSTRACT

A tourniquet for restricting the flow of blood to and from a limb of an individual when assembled thereon, the tourniquet having a flexible and resilient elongated member and a tourniquet securing member fixedly secured to one end of the flexible and resilient elongated member and having an aperture therethrough to receive a second end of the elongated member once the elongated member is wrapped about the limb of an individual so that the second end of the elongated member can be pulled against the inner peripheral surface of the aperture causing the tourniquet securing member to bear against the individual's limb and the tightening of the elongated member about the limb so as to enlarge and expose the veins or veinlets of the limb. The tourniquet securing member includes a cavity at one end to receive the elongated member wherein the cavity has gripping teeth therein to fixedly grip the flexible and resilient elongated member.

11 Claims, 3 Drawing Sheets

TOURNIQUET

BACKGROUND OF THE INVENTION

The present invention relates to tourniquets adapted to be wrapped tightly about the limb of an individual to restrict the flow of blood to and from the limb thereby permitting the blood in an open cut to clot or to cause a veinlet to enlarge and become exposed at the surface of the limb.

Tourniquets for restricting the flow of blood in the above-described manner have been in use for centuries. The general concept underlying the use of tourniquets has been practiced in several different ways utilizing several different implements. Typically, an elongated piece of rope, cloth or the like has been wrapped about the limb of an individual and tightened by either knotting the same or rotating a rigid member which has been secured to the elongated rope or cloth. Velcro fastening means have also been employed to fix the elongated rope or cloth to the limb in a tightened arrangement. Other more sophisticated devices serve a similar purpose. For instance, the typical blood pressure indicating device comprises a flat elongated and inflatable member which is fastened to the upper arm by Velcro fasteners. Once inflated, this device restricts the flow of blood to and from the arm so that the pulsations therein can be monitored on a pressure-indicating instrument.

The present invention seeks to provide a tourniquet which is simply structured and easily applied to the limb of an individual to restrict the flow of blood to the limb, thereby enlarging and exposing veins or veinlets in the limb for the withdrawal of blood therefrom, the introduction of a medicinal fluid into a veinlet or to enhance the clotting of blood in an open cut on the limb.

SUMMARY OF THE INVENTION

In accordance with the present invention, a tourniquet is provided for restricting the flow of blood to the limb of an individual when wrapped thereabout, the tourniquet having a flexible elongated member with a first end, a second end and an intermediate portion between said first end and said second end remote from said first end, and tourniquet securing means fixed to said first end of the flexible elongated member and having an aperture therethrough to receive said second end of said flexible elongated member after said elongated member is assembled on the limb of an individual so that said elongated member can be tightened about said limb upon pulling said second end away from said first end and against said elongated member. The tourniquet securing means includes a first member mateably secured to a second member, both of which members have recess means with gripping means therein to fixedly attach said first end of said elongated member to said tourniquet securing means. A first member and second member further include guide pin means for aligning said first member on said second member prior to attachment and for providing additional strength in the longitudinal direction of the tourniquet securing means.

Accordingly, it is an object of the present invention to provide a tourniquet having a flexible elongated member for wrapping about the limb of an individual and a simply structured tourniquet securing means fixed to one end of the elongated member to facilitate the tightening of the elongated member about the limb of an individual.

It is another object of the present invention to provide a tourniquet which utilizes conventional rubber surgical tubing or like materials for the elongated member and tourniquet securing means with gripping means particularly adapted to grip and thereby fix the conventional surgical tubing within the tourniquet securing means.

It is yet another object of the present invention to provide a tourniquet which is particularly adapted to be wrapped tightly about the limb of an individual so as to restrict the flow of blood to and from the limb of an individual, thereby enlarging and exposing a veinlet for withdrawing blood or introducing medicinal fluids, or to enhance the clotting of blood in an open cut on said limb.

These and other objects will become apparent, as will a better understanding of the concepts underlying the present invention, by reference to the description which follows when taken in conjunction with the accompanying drawings.

DETAILED DESCRIPTION OF THE INVENTION

Figure 1:
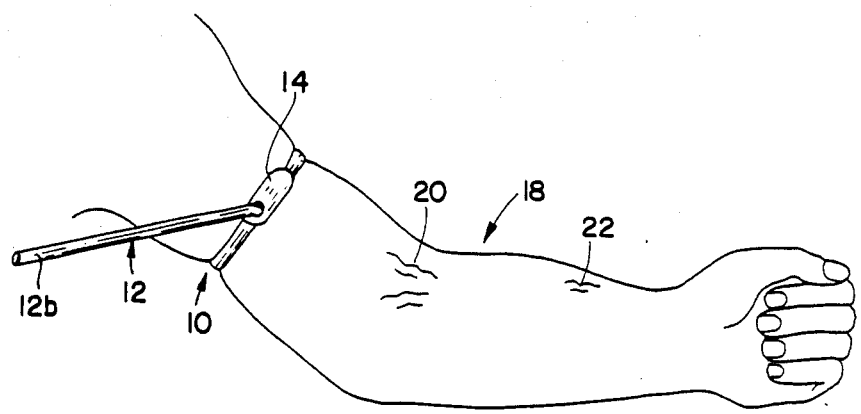
FIG. 1 is a perspective view of the limb of an individual with a tourniquet in accordance with the present invention wrapped tightly thereabout so as to enlarge and expose veinlets in the medial region of the arm depicted therein.
Figure 2:
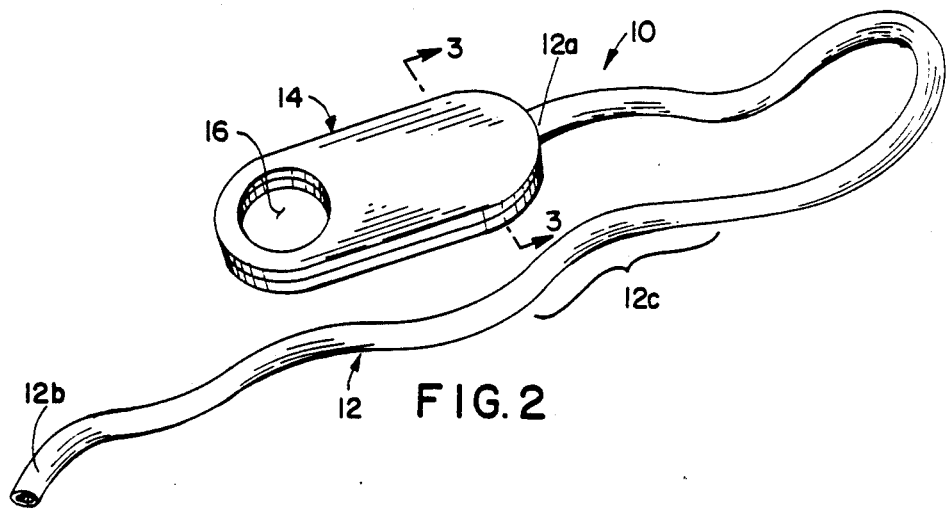
FIG. 2 is a perspective view of a tourniquet in accordance with the present invention.

Referring to the drawings, FIGS. 1 and 2 illustrate the preferred embodiment of the tourniquet generally designated as 10 in accordance with the present invention. The remaining Figures illustrate a preferred embodiment of the tourniquet securing means which comprises a part of the tourniquet in accordance with the present invention, illustrating in particular the structure utilized to fixedly secure the elongated member of the tourniquet 10 to the tourniquet securing means.

The tourniquet 10 generally comprises a flexible and resilient elongated member 12 having a first end 12a, a second end 12b and an intermediate portion 12c disposed between said first end 12a and said second end 12b, and tourniquet securing means 14 fixedly secured to said first end 12a of said elongated member 12. Tourniquet securing means 14 is preferably made of any suitable plastic and includes aperture 16 to receive said second end 12b on said elongated member 12 and a longitudinal axis generally parallel or the same as the longitudinal axis of elongated member 12 at the attachment point between tourniquet securing means 14 and first end 12a.

FIG. 1 shows the tourniquet 10 assembled on the upper arm of arm 18, wherein intermediate portion 12c of elongated member 12 is wrapped about the upper arm and second end 12b of elongated member 12 is disposed through aperture 16 of tourniquet securing means 14. Thus, when second end 12b of elongated member 12 is pulled away from first end 12a of elongated member 12 in a direction parallel to the longitudinal axis of tourniquet securing means 14 and against the inner peripheral surface of aperture 16, elongated member 12 tightens about the upper arm of arm 18 to prevent the flow of blood back to the heart through the one-way valves in the veins or veinlets, thereby enlarging and exposing veins or veinlets 20 in the medial region of arm 18 (between the upper arm and the forearm). Elongated member 12 can be temporarily fixed in such an arrangement on arm 18 by knotting the same or by any suitable temporary fastening means (not shown), or elongated member 12 can be held in such tightened arrangement by the individual or physician's assistant. Once such veinlets 20 are exposed, it is possible to extract blood from arm 18 or introduce medicinal fluids into arm 18. Tourniquet 10 might also be used, in conjunction with localized pressure, to enhance the clotting of blood in an open cut 22, if such open cut is not too large. Of course, tourniquet 10 can be assembled on any limb of an individual to restrict the flow of blood to and from that limb or an extremity of that limb (hand, feet).

Figure 3:
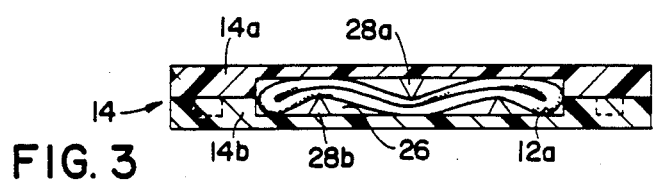
FIG. 3 is a cross-sectional view taken on line 3—3 of FIG. 2, illustrating in particular the gripping structure of the tourniquet securing means.

FIG. 3 is a cross-sectional view of the tourniquet securing means at the point of attachment between first end 12a of elongated member 12 and tourniquet securing means 14. Thus, it can be seen that tourniquet securing means comprises a top plate 14a and a bottom plate 14b. FIG. 3 further illustrates the particular gripping arrangement employed to secure first end 12a of elongated member 12 to tourniquet securing means 14. FIGS. 3–9 show top plate 14a and bottom plate 14b include openings at one end and recess means 24a and 24b, respectively, which are in communication with said openings. Once top plate 14a is mateably secured to bottom plate 14b, the openings thereof together form a larger opening to receive first end 12a of elongated member 12 into a cavity 26 defined by recess means 24a and 24b. The gripping means provided in recess means 24a and 24b comprise a plurality of teeth 28a and 28b, respectively, which protrude in opposite lateral directions into cavity 26 to grippedly secure first end 12a of elongated member 12, as shown in FIG. 3.

Top plate 14a includes an aperture 16a and bottom plate 14b includes an aperture 16b, which together form aperture 16 when top plate 14a is secured to bottom plate 14b. An annular protrusion 30 is provided on top plate 14a about aperture 16a. Annular protrusion 30 is received within annular groove 32 formed about aperture 16b of bottom plate 14b. Top plate 14a further includes six guide pins 34 about recess means 24a. These guide pins 34 are situated to be alignedly received into the six pin depressions 36 provided about recess means 24b of bottom plate 14b. Annular protrusion 30, annular groove 32, guide pins 34 and depressions 36 facilitate the alignment of top plate 14a and bottom plate 14b prior to the securement thereof. These elements further provide a considerable degree of strength in the longitudinal direction, thereby reducing the shear forces effectuated upon the tourniquet securing means 14 when second end 12b of elongated member 12 is pulled in a longitudinal direction to tighten tourniquet 10 about the limb of an individual as explained above.

Figure 4:
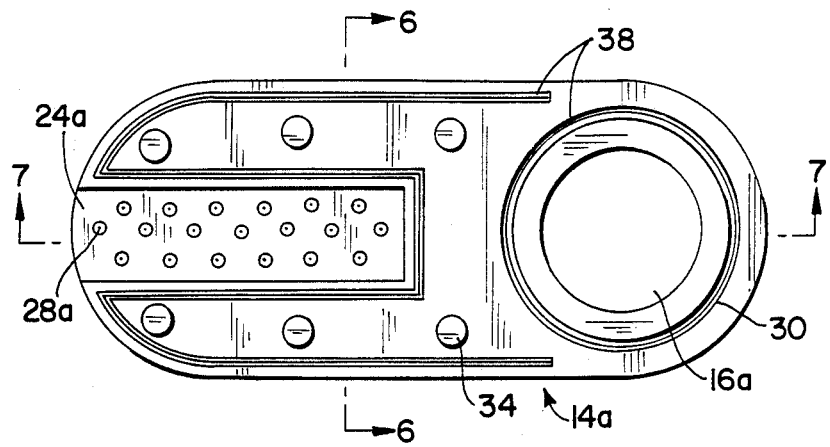
FIG. 4 is a plan view of the interior surface of the top plate of the tourniquet securing means of the present invention.
Figure 5:
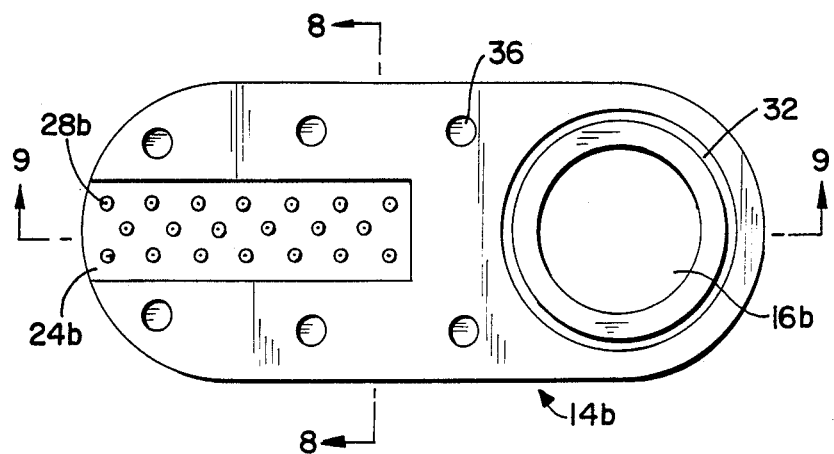
FIG. 5 is a plan view of the interior surface of the bottom plate of the tourniquet securing means of the present invention.
Figure 6:
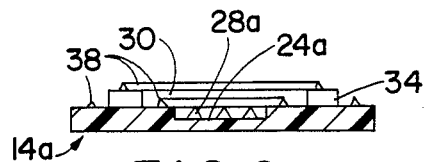
FIG. 6 is a cross-sectional view of the top plate of the tourniquet securing means taken on line 6—6 in FIG. 4.
Figure 7:
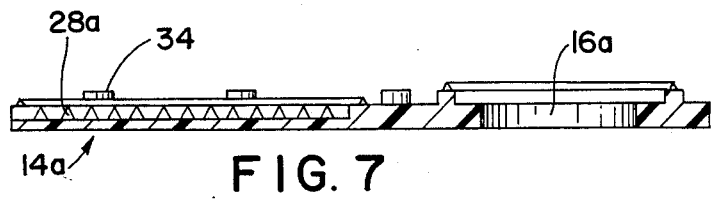
FIG. 7 is a cross-sectional view of the top plate of the tourniquet securing means taken on line 7—7 of FIG. 4.
Figure 8:
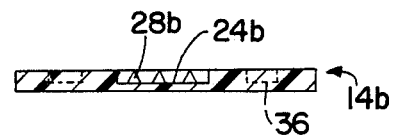
FIG. 8 is a cross-sectional view of the bottom plate of the tourniquet securing means taken on line 8—8 of FIG. 5.
Figure 9:
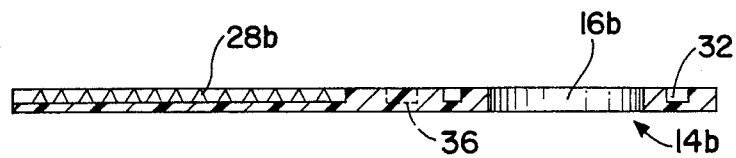
FIG. 9 is a cross-sectional view of the bottom plate of the tourniquet securing means taken on line 9—9 of FIG. 5.

While any suitable means may be employed to secure top plate 14a to bottom plate 14b, the preferred embodiment of the present invention employs a sonic-welding technique. Thus, sonic energizers 38 are provided at specific areas on top plate 14a. FIG. 4 shows sonic energizers 38 disposed on the upper surface of annular protrusion 30, about the peripheral surfaces of top plate 14a and about recess means 24a of top plate 14a. In cross-section, sonic energizers 38 are in the shape of an inverted "v" having an apex which is approximately 0.015 inches from the surface on which sonic energizers 38 are situated and are defined by an included angle of 60°. As a reference as to the relative size of energizers 38, protrusion 30 is approximately 0.031 inches in height from the lower surface of top plate 14a. Thus, once top plate 14a and bottom plate 14b are aligned for securement, with first end 12a of elongated member 12 disposed in cavity 26 and clamped between teeth 28a and 28b, the aligned arrangement is subjected to compression and ultrasonic vibrations. The ultrasonic vibrations create a friction force at sonic energizers 38 to melt the plastic energizers and thereby join the interior surfaces of top plate 14a and bottom plate 14b. Once the desired melting has occurred, energy flow creating the ultrasonic vibrations is terminated, and top plate 14a and bottom plate 14b are permitted to remain briefly between the compression platens or other devices utilized to facilitate the compression so that the joint between the surfaces can set. As one skilled in the art will recognize, an ultrasonic assembly process is extremely quick and yields bond strengths which closely approximate the strength of the parent materials.

It is to be noted that tourniquet securing means 14 can be of any shape or size which is conducive to the use of tourniquet 10 as explained above and shown in FIG. 1. Thus, tourniquet securing means 14 could be circular, rectangular or oval and aperture 16 thereof can be provided at any portion thereof. In the preferred embodiment, tourniquet securing means 14 is generally elongated and is provided with aperture 16 at the end remote from first end 12a of elongated member 12. It has been found that this arrangement is particularly conducive to the use described above and shown in FIG. 1 inasmuch as the elongated portion of tourniquet securing means 14 bears against the upper arm or other limb in the crosswise direction when second end 12b of elongated member 12 is pulled away from first end 12a in the longitudinal direction of tourniquet securing means 14 and against the inner peripheral surface of aperture 16.

The preferred embodiment of tourniquet 10 further comprises tourniquet securing means 14 which is particularly adapted to accommodate conventional 3/16 inch OD surgical tubing.

Thus, a tourniquet for restricting the flow of blood to and from a limb of an individual so as to enlarge and expose veins and veinlets thereby permitting the withdrawal of blood, the introduction of medicinal fluids, or enhancing the clotting of blood in a cut on the limb has been described.

While the foregoing description and Figures illustrate one preferred embodiment of the tourniquet in accordance with the present invention, it should be appreciated that certain modifications may be made without departing from the spirit and scope of the invention envisioned by the inventor herein and as defined by the claims which are set forth immediately below.

What is claimed:

1. A tourniquet for restricting the flow of blood to and from the limb of an individual when assembled thereon, said tourniquet comprising, an elongate member having a first end, a second end from said first end, an intermediate portion disposed between said first end and said second end and a longitudinal axis, said elongate member being adapted for wrapping about the limb of an individual, tourniquet securing means having one end attached to said first end of said elongate member and having a longitudinal axis coinciding with said longitudinal axis of said tourniquet securing means having an aperture therethough, said aperture having an inner peripheral surface and being adapted to receive said second end of said elongate member after said elongate member is wrapped about the limb of an individual so that said second end of said elongate member can be pulled away from said first end in the longitudinal direction and against said inner peripheral surface of said aperture thereby tightening said elongate member about said limb, said tourniquet securing means including a first member and a second member, said first member being mateably secured to said second member, said first member having a first opening at one end thereof and first recess means in communication with said first opening, said second member having a second opening adjacent said first opening and second recess means in communication with said second opening, said second recess means being adjacent said first recess means to form a recess, said recess and said first and second openings being adapted to receive said first end of said elongate member, said first and second recess means being situated remote from said aperture and having gripping means therein to fixedly attach said first end of said elongate member to said tourniquet securing means upon securement of said first member to said second member.

2. The tourniquet claimed in claim 1, wherein said elongate member is flexible and resilient.

3. The tourniquet claimed in claim 2, wherein said elongate member comprises conventional surgical tubing.

4. The tourniquet claimed in claim 1, wherein said first member and second member are secured to one another by ultrasonic vibration.

5. The tourniquet claimed in claim 1, wherein said first member includes at least one guide pin and said second member includes at least one pin depression for receiving said guide pin of said first member, thereby facilitating the proper alignment of said first member and said second member during assembly thereof and providing additional strength to said tourniquet securing means in the longitudinal direction thereof.

6. A tourniquet for restricting the flow of blood to and from the limb of an individual when assembled thereon, said tourniquet comprising, an elongate member having a first end, a second end remote from said first end, an intermediate portion disposed between said first end and said second end and a longitudinal axis, said elongate member being adapted for wrapping about the limb of an individual, tourniquet securing means attached to said first end of said elongate member and having a longitudinal axis coinciding with said longitudinal axis of said elongate member at said first end, said tourniquet securing means being adapted to facilitate the securement of said elongate member after said elongate member is wrapped about the limb of an individual and pulled away from said first end in the longitudinal direction thereby tightening said elongate member about said limb, said tourniquet securing means including a first member and a second member, said first member being mateably secured to said second member, said first member having a first opening at one end thereof and first recess means in communication with said first opening, said second member having a second opening adjacent said first opening and second recess means in communication with said second opening, said second recess means being adjacent said first recess means to form a recess, said recess and said first and second openings being adapted to receive said first end of said elongate member, said first and second recess means having gripping means therein to fixedly attach said first end of said elongate member to said tourniquet securing means upon securement of said first member to said second member.

7. The tourniquet claimed in claim 6, wherein said elongate member is flexible and resilient.

8. The tourniquet claimed in claim 7, wherein said elongate member comprises conventional surgical tubing.

9. The tourniquet claimed in claim 7, wherein said recess means is elongate.

10. The tourniquet claimed in claim 6, wherein said first member and said second member are secured to one another by ultrasonic vibration.

11. The tourniquet claimed in claim 6, wherein said first member includes at least one guide pin and said second member includes at least one pin depression for receiving said guide pin of said first member, thereby facilitating the proper alignment of said first member and said second member during assembly thereof and providing additional strength to said tourniquet securing means in the longitudinal direction thereof.

* * * * *